(12) United States Patent
Itoh et al.

(10) Patent No.: US 6,664,232 B1
(45) Date of Patent: Dec. 16, 2003

(54) HLA-A2 RESTRAINT TUMOR ANTIGEN PEPTIDE ORIGINATING IN SART-1

(75) Inventors: Kyogo Itoh, Saga (JP); Terutada Kobayashi, Saitama (JP)

(73) Assignees: Kyogo Itoh, Saga-ken (JP); Sumitomo Pharmaceuticals Company, Limited, Osaka-fu (JP)

( * ) Notice: Subject to any disclaimer, the term of this patent is extended or adjusted under 35 U.S.C. 154(b) by 0 days.

(21) Appl. No.: 09/744,549

(22) PCT Filed: Jul. 27, 1999

(86) PCT No.: PCT/JP99/04010

§ 371 (c)(1),
(2), (4) Date: Feb. 26, 2001

(87) PCT Pub. No.: WO00/06595

PCT Pub. Date: Feb. 10, 2000

(30) Foreign Application Priority Data

Jul. 28, 1998 (JP) ............................................. 10-212940

(51) Int. Cl.$^7$ ................................................. A61L 38/00
(52) U.S. Cl. ......................... 514/16; 530/377; 530/328; 514/0.5
(58) Field of Search ................ 530/324–328, 530/350, 300; 514/12–16

(56) References Cited

U.S. PATENT DOCUMENTS 5,554,724 A    9/1996    Melief et al.

FOREIGN PATENT DOCUMENTS

| EP | 0911397 A1 | 4/1999 |
| EP | 1055684 A1 | 11/2000 |
| EP | 1 097 940 A1 | 5/2001 |
| WO | A1-9746676 | 12/1997 |
| WO | A1-9929715 | 6/1999 |

OTHER PUBLICATIONS

Lazar et al Mol. Cell. Biol. vol. 8 p. 1247 (1988).*
Schwartz et al PNAS vol. 84 p. 6408 (1987).*
Burgess et al J. Cell Biol. vol. 111 p. 2129 (1990).*
Lin et al Biochem. vol. 14 p. 1559 (1975).*
Johnson et al, Cancer Treatment Reviews vol. 2 p. 1 (1975).*
Valenta, J. Investigative Dermatology vol. 111 p. 1178(1998).*
Shichijo et al., J. Exp. Med., vol. 187, No. 3, pp. 277–288 (1998).
Nakao et al., Cancer res. vol. 55, No. 19, pp. 4248–4252 (1995).
Rivoltini et al., J. Immunol. vol. 154. No. 5, pp. 2257–2265 (1995).
Rammensee et al., Immunogenetics, vol. 41, No. 4, pp. 178–228 (1995).
Sudo et al., J. Immunol., vol. 155, No. 10, pp. 4749–4756 (1995).
Kikuchi et al., Int. J. Cancer, vol. 81, No. 3, pp. 459–466 (1999).
J.Exp.Med., vol. 187, No. 3, pp. 277–288 (1998); S. Shichijo et al.
Cancer Res., vol. 55, No. 19, pp. 4248–4252 (1995); M. Nakao et al.
J.Immunol., vol. 154, No. 5, pp. 2257–2265 (1995); L. Rivoltini et al.
Int.J.Cancer, vol. 58, pp. 317–323 (1994); D. D. Karkevitch et al.
Immunogenetics, vol. 41, pp. 178–228 (1995); H.–G. Rammensee et al.
J.Immunol., vol. 160, pp. 1717–1723 (1998); S.A. Thomson et al.
J. Immunol., vol. 158, pp. 1796–1802 (1997); Van Tsai et al.
Science, vol. 274, pp. 94–96 (1996); John D. Altman et al.
NCBI Sequence Viewer, M84379 (1995).
Int.J.Cancer, vol. 81, pp. 459–466 (1999); Megumi Kikuchi et al.
J. of Natl. Cancer Inst., vol. 86, No. 15, pp. 1159–1166 (1994); S.A.Rosenberg et al.

* cited by examiner

*Primary Examiner*—Sheela Huff
(74) *Attorney, Agent, or Firm*—Birch, Stewart, Kolasch & Birch, LLP

(57) ABSTRACT

An HLA-A2 restricted tumor antigen peptide originated fromr SART-1, derivatives thereof having characteristics functionally equivalent thereto; therapeutic, prophylactic or diagnostic agents for tumors which utilize the tumor antigen peptide or its derivative, a recombinant DNA, recombinant polypeptide or antibody related to said tumor antigen peptide, or use thereof; an antigen presenting cell presenting the said tumor antigen peptide or use thereof; cytotoxic T lymphocyte specific for said tumor antigen peptide or use thereof.

7 Claims, No Drawings

```
                            SEQUENCE LISTING

<160> NUMBER OF SEQ ID NOS: 40

<210> SEQ ID NO 1
<211> LENGTH: 9
<212> TYPE: PRT
<213> ORGANISM: Homo sapiens

<400> SEQUENCE: 1

Leu Leu Leu Cys Gln Asn Lys Gly Leu
                 5

<210> SEQ ID NO 2
<211> LENGTH: 10
<212> TYPE: PRT
<213> ORGANISM: Homo sapiens

<400> SEQUENCE: 2

Leu Leu Leu Cys Gln Asn Lys Gly Leu Leu
                 5                  10

<210> SEQ ID NO 3
<211> LENGTH: 9
<212> TYPE: PRT
<213> ORGANISM: Homo sapiens

<400> SEQUENCE: 3

Leu Leu Glu Thr Thr Val Gln Lys Val
                 5

<210> SEQ ID NO 4
<211> LENGTH: 9
<212> TYPE: PRT
<213> ORGANISM: Homo sapiens

<400> SEQUENCE: 4

Arg Val Lys Ala Pro Asn Lys Ser Leu
                 5

<210> SEQ ID NO 5
<211> LENGTH: 9
<212> TYPE: PRT
<213> ORGANISM: Homo sapiens

<400> SEQUENCE: 5

Tyr Val Asp Glu Thr Gly Arg Lys Leu
                 5

<210> SEQ ID NO 6
<211> LENGTH: 9
<212> TYPE: PRT
<213> ORGANISM: Homo sapiens
```

```
<400> SEQUENCE: 6

Ala Gln Lys Thr Pro Tyr Ile Val Leu
                  5

<210> SEQ ID NO 7
<211> LENGTH: 9
<212> TYPE: PRT
<213> ORGANISM: Homo sapiens

<400> SEQUENCE: 7

Ile Leu Thr Leu Lys Asp Lys Gly Val
                  5

<210> SEQ ID NO 8
<211> LENGTH: 9
<212> TYPE: PRT
<213> ORGANISM: Homo sapiens

<400> SEQUENCE: 8

Val Leu Gln Glu Glu Glu Asp Val Leu
                  5

<210> SEQ ID NO 9
<211> LENGTH: 9
<212> TYPE: PRT
<213> ORGANISM: Homo sapiens

<400> SEQUENCE: 9

Leu Gln Glu Glu Glu Asp Val Leu Val
                  5

<210> SEQ ID NO 10
<211> LENGTH: 9
<212> TYPE: PRT
<213> ORGANISM: Homo sapiens

<400> SEQUENCE: 10

Ile Leu Ser Lys Tyr Asp Glu Glu Leu
                  5

<210> SEQ ID NO 11
<211> LENGTH: 9
<212> TYPE: PRT
<213> ORGANISM: Homo sapiens

<400> SEQUENCE: 11

Glu Gln Gly Gly Thr Ala Asp Gly Leu
                  5

<210> SEQ ID NO 12
<211> LENGTH: 9
<212> TYPE: PRT
<213> ORGANISM: Homo sapiens

<400> SEQUENCE: 12

Lys Leu Arg Leu Gln Ala Gln Ser Leu
                  5

<210> SEQ ID NO 13
<211> LENGTH: 9
<212> TYPE: PRT
<213> ORGANISM: Homo sapiens

<400> SEQUENCE: 13
```

Leu Gln Ala Gln Ser Leu Ser Thr Val
                  5

<210> SEQ ID NO 14
<211> LENGTH: 9
<212> TYPE: PRT
<213> ORGANISM: Homo sapiens

<400> SEQUENCE: 14

Ser Leu Ser Thr Val Gly Pro Arg Leu
                  5

<210> SEQ ID NO 15
<211> LENGTH: 9
<212> TYPE: PRT
<213> ORGANISM: Homo sapiens

<400> SEQUENCE: 15

Val Val Val Arg Ala Asp Asp Leu Leu
                  5

<210> SEQ ID NO 16
<211> LENGTH: 9
<212> TYPE: PRT
<213> ORGANISM: Homo sapiens

<400> SEQUENCE: 16

Pro Leu Pro Ser Asp Asp Thr Arg Val
                  5

<210> SEQ ID NO 17
<211> LENGTH: 9
<212> TYPE: PRT
<213> ORGANISM: Homo sapiens

<400> SEQUENCE: 17

Val Leu Glu Glu Asp Glu Ala Glu Leu
                  5

<210> SEQ ID NO 18
<211> LENGTH: 9
<212> TYPE: PRT
<213> ORGANISM: Homo sapiens

<400> SEQUENCE: 18

Lys Gln Leu Glu Lys Gly Arg Arg Leu
                  5

<210> SEQ ID NO 19
<211> LENGTH: 9
<212> TYPE: PRT
<213> ORGANISM: Homo sapiens

<400> SEQUENCE: 19

Arg Gln Leu Gln Gln Leu Gln Gln Leu
                  5

<210> SEQ ID NO 20
<211> LENGTH: 9
<212> TYPE: PRT
<213> ORGANISM: Homo sapiens

<400> SEQUENCE: 20

Gln Leu Arg Asp Ser Gly Glu Lys Val

```
<210> SEQ ID NO 21
<211> LENGTH: 9
<212> TYPE: PRT
<213> ORGANISM: Homo sapiens

<400> SEQUENCE: 21

Lys Leu Gly Leu Lys Pro Leu Glu Val
                 5

<210> SEQ ID NO 22
<211> LENGTH: 9
<212> TYPE: PRT
<213> ORGANISM: Homo sapiens

<400> SEQUENCE: 22

Thr Leu Gly Glu Asp Asp Pro Trp Leu
                 5

<210> SEQ ID NO 23
<211> LENGTH: 9
<212> TYPE: PRT
<213> ORGANISM: Homo sapiens

<400> SEQUENCE: 23

Arg Gln Leu Gln Lys Glu Lys Asp Leu
                 5

<210> SEQ ID NO 24
<211> LENGTH: 9
<212> TYPE: PRT
<213> ORGANISM: Homo sapiens

<400> SEQUENCE: 24

Asp Leu Ala Glu Lys Arg Ala Lys Leu
                 5

<210> SEQ ID NO 25
<211> LENGTH: 9
<212> TYPE: PRT
<213> ORGANISM: Homo sapiens

<400> SEQUENCE: 25

Asp Gln Glu Phe Gly Val Ser Thr Leu
                 5

<210> SEQ ID NO 26
<211> LENGTH: 9
<212> TYPE: PRT
<213> ORGANISM: Homo sapiens

<400> SEQUENCE: 26

Gly Val Leu Gln Glu Glu Glu Asp Val
                 5

<210> SEQ ID NO 27
<211> LENGTH: 9
<212> TYPE: PRT
<213> ORGANISM: Homo sapiens

<400> SEQUENCE: 27

Asp Val Leu Val Asn Val Asn Leu Val
                 5
```

<210> SEQ ID NO 28
<211> LENGTH: 9
<212> TYPE: PRT
<213> ORGANISM: Homo sapiens

<400> SEQUENCE: 28

Ala Gln Gln Lys Pro Arg Ser Ile Leu
                5

<210> SEQ ID NO 29
<211> LENGTH: 9
<212> TYPE: PRT
<213> ORGANISM: Homo sapiens

<400> SEQUENCE: 29

Glu Leu Glu Glu Ile Arg Ala Lys Leu
                5

<210> SEQ ID NO 30
<211> LENGTH: 9
<212> TYPE: PRT
<213> ORGANISM: Homo sapiens

<400> SEQUENCE: 30

Glu Val Val Val Arg Ala Asp Asp Leu
                5

<210> SEQ ID NO 31
<211> LENGTH: 9
<212> TYPE: PRT
<213> ORGANISM: Homo sapiens

<400> SEQUENCE: 31

Glu Val Glu Glu Glu Lys Glu Pro Val
                5

<210> SEQ ID NO 32
<211> LENGTH: 9
<212> TYPE: PRT
<213> ORGANISM: Homo sapiens

<400> SEQUENCE: 32

Lys Val Val Glu Ile Val Lys Lys Leu
                5

<210> SEQ ID NO 33
<211> LENGTH: 9
<212> TYPE: PRT
<213> ORGANISM: Homo sapiens

<400> SEQUENCE: 33

Asn Ile Gly Trp Ser Thr Val Asn Leu
                5

<210> SEQ ID NO 34
<211> LENGTH: 9
<212> TYPE: PRT
<213> ORGANISM: Homo sapiens

<400> SEQUENCE: 34

Lys Met Ser Ser Ser Asp Thr Pro Leu
                5

<210> SEQ ID NO 35

```
<211> LENGTH: 9
<212> TYPE: PRT
<213> ORGANISM: Artificial Sequence
<220> FEATURE:
<223> OTHER INFORMATION: Variant Peptide derived from Homo sapiens.
<221> NAME/KEY: VARIANT
<222> LOCATION: 2
<223> OTHER INFORMATION: Xaa is Leu, Met, Val, Ile or Gln.
<221> NAME/KEY: VARIANT
<222> LOCATION: 9
<223> OTHER INFORMATION: Xaa is Val or Leu.

<400> SEQUENCE: 35

Leu Xaa Leu Cys Gln Asn Lys Gly Xaa
                5

<210> SEQ ID NO 36
<211> LENGTH: 10
<212> TYPE: PRT
<213> ORGANISM: Artificial Sequence
<220> FEATURE:
<223> OTHER INFORMATION: Variant Peptide derived from Homo sapiens.
<221> NAME/KEY: VARIANT
<222> LOCATION: 2
<223> OTHER INFORMATION: Xaa is Leu, Met, Val, Ile or Gln.
<221> NAME/KEY: VARIANT
<222> LOCATION: 10
<223> OTHER INFORMATION: Xaa is Val or Leu.

<400> SEQUENCE: 36

Leu Xaa Leu Cys Gln Asn Lys Gly Leu Xaa
                5                   10

<210> SEQ ID NO 37
<211> LENGTH: 9
<212> TYPE: PRT
<213> ORGANISM: Artificial Sequence
<220> FEATURE:
<223> OTHER INFORMATION: Variant Peptide derived from Homo sapiens.
<221> NAME/KEY: VARIANT
<222> LOCATION: 2
<223> OTHER INFORMATION: Xaa is Leu, Met, Val, Ile or Gln.
<221> NAME/KEY: VARIANT
<222> LOCATION: 9
<223> OTHER INFORMATION: Xaa is Val or Leu.

<400> SEQUENCE: 37

Leu Xaa Glu Thr Thr Val Gln Lys Xaa
                5

<210> SEQ ID NO 38
<211> LENGTH: 9
<212> TYPE: PRT
<213> ORGANISM: Artificial Sequence
<220> FEATURE:
<223> OTHER INFORMATION: Variant Peptide derived from Homo sapiens.
<221> NAME/KEY: VARIANT
<222> LOCATION: 2
<223> OTHER INFORMATION: Xaa is Leu, Met, Val, Ile or Gln.
<221> NAME/KEY: VARIANT
<222> LOCATION: 9
<223> OTHER INFORMATION: Xaa is Val or Leu.

<400> SEQUENCE: 38

Arg Xaa Lys Ala Pro Asn Lys Ser Xaa
                5

<210> SEQ ID NO 39
<211> LENGTH: 9
<212> TYPE: PRT
<213> ORGANISM: Artificial Sequence
```

```
-continued

<220> FEATURE:
<223> OTHER INFORMATION: Variant Peptide derived from Homo sapiens.
<221> NAME/KEY: VARIANT
<222> LOCATION: 2
<223> OTHER INFORMATION: Xaa is Leu, Met, Val, Ile or Gln.
<221> NAME/KEY: VARIANT
<222> LOCATION: 9
<223> OTHER INFORMATION: Xaa is Val or Leu.

<400> SEQUENCE: 39

Tyr Xaa Asp Glu Thr Gly Arg Lys Xaa
                5

<210> SEQ ID NO 40
<211> LENGTH: 9
<212> TYPE: PRT
<213> ORGANISM: Artificial Sequence
<220> FEATURE:
<223> OTHER INFORMATION: Variant Peptide derived from Homo sapiens.
<221> NAME/KEY: VARIANT
<222> LOCATION: 2
<223> OTHER INFORMATION: Xaa is Leu, Met, Val, Ile or Gln.
<221> NAME/KEY: VARIANT
<222> LOCATION: 9
<223> OTHER INFORMATION: Xaa is Val or Leu.

<400> SEQUENCE: 40

Ala Xaa Lys Thr Pro Tyr Ile Val Xaa
                5
```

HLA-A2 RESTRAINT TUMOR ANTIGEN PEPTIDE ORIGINATING IN SART-1

This application is the national phase under 35 U.S.C. § 371 of PCT International Application No. PCT/JP99/04010 which has an International filing date of Jul. 27, 1999, which designated the United States of America.

TECHNICAL FIELD

The present invention relates to HLA-A2 restricted tumor antigen peptide originated fom SART-1. More particularly, the present invention relates to an HLA-A2 restricted tumor antigen peptide originated from SART-1, derivatives thereof having characteristics functionally equivalent thereto, compositions for treating, preventing or diagnosing tumors which utilize the tumor antigen peptide or its derivative in vivo or in vitro.

BACKGROUND ART

It is known that the immune system, particularly T cells, plays an important role in uivo in tumor rejection. Indeed, infiltration of lymphocytes having cytotowic effects on tumor cells has been observed in human tumor foci (*Arch. Surg.*, 126: 200, 1990), and cytotoxic T lymphocytes (CTILs) recognizing autologous tumor cells have been isolated from melanomas without great difficulties (e.g., *Immunol. Today*, 8:385, 1987; *J. Immurnol.*, 138:989, 1987; and *Int. J. Cancer*, 52: 52, 1992). In addition, the results of clinical treatment of melanomas by CTL introduction also suggest the importance of T cells in tumor rejection (*J. Natl. Cancer. Inst.*, 86: 1159, 1994).

Although it has long been unknown about target molecules for CTLs attacking autologous tumor cells, the recent advance in immunology and molecular biology has gradually revealed such target molecules. Specifically, it has been found that using T cell receptors (TCRs), CTL recognizes a complex between a peptide, called tumor antigen peptide, and a major histocompatibility complex class I antigen (MHC class I antigen, and in the case of human, referred to as HLA antigen), and thereby attacks autologous tumor cells.

Tumor antigen peptides are generated from proteins specific for tumors, that is, tumor antigen proteins. Thus, the proteins are intracellularly synthesized and then processed in cytoplasm into the peptides by proteasome. The resultant tumor antigen peptides form a complex with MHC class I antigens (HLA antigens) in endoplasmic reticulum and transported to the cell surface where they are presented as antigen. A tumor-specific CTL recognizes the complex presented as an antigen, and exhibits the anti-tumor effects through the cytotoxc effect or the production of lymphokines. As a consequence of such elucidation of a series of actions, it has become possible to treat tumors by using tumor antigen proteins or tumor antigen peptides as so-called cancer vaccines, which enhance tumor-specific CTLs in a patient.

As such tumor antigen proteins, T. Boon et al. identified a protein named MAGE from human melanoma cells for the first time in 1991 (*Science*, 254: 1643, 1991), and thereafter several additional tumor antigen proteins have been identified from melanoma cells. Examples of melanoma antigens identified so far include melanocyte tissue specific proteins, for instance, gp100 (*J. Em. Med.*, 179:1005, 1994), MART-1 (*Proc. Natl. Acad Sci. USA*, 91:3515, 1994), melanosome proteins such as tyrosinase (*J. Ex. Med.*, 178:489, 1993); MAGE-related proteins expressed in various tumor cells and normal testis cells as well as melanomas (*J. Em. Med.*, 179:921, 1994); those comprising tumor-specific mutations such as β-catenin (*J. E. Med.*, 183:1185, 1996), CDK4 (*Science*, 269:1281, 1995) and the like. Further, tumor antigen proteins other than melanomas, which have been identified so far, include oncogene products such as HER2/neu (*J. Ekg. Med.*, 181: 2109, 1995), p53 (mutant) (*Pror Natl. Acad. Sci. USA*, 93: 14704, 1996) and the like; tumor markers such as CEA (*J. Natl. Cancer. Inst.*, 87: 982, 1995), PSA (*J. Natl. Cancer. Inst.*, 89: 293, 1997); viral proteins such as HPV (*J. Immunol.*, 154: 5934, 1995), EBV (*Int. Immunol.*, 7: 653, 1995), and the like. The detail of these tumor antigens is provided in reviews (*Immunol. Today*, 18: 267, 1997; *J. Exp. Med.*, 183: 725, 1996; *Curr. Opin. Immunol.*, 8: 628, 1996, etc.)

To apply tumor antigen proteins or peptides to the treatment or diagnosis of tumors, it is important to identify tumor antigens widely applicable to tumors of much higher incidence than melanomas, for example, squamous cell carcinomas (e.g., esophageal cancer, lung cancer). In this connection, the present inventors have conducted cloning of a gene encoding a tumor antigen protein from squamous cell carcinoma cells derived from esophageal cancer. The inventors, for the first time, cloned a gene encoding a novel tumor antigen protein ("SART-1") from tumor cells other than melanomas, and identified certain tumor antigen peptide portions from said SART-1, which can be presented after binding to HLA-A26 or HLA-A24 antigen (*J. Exp. Med.*, 187: 277, 1998, WO97/46676).

However, it has not been known whether said SART-1 comprises tumor antigen peptide portions capable of binding to HLA-A2 antigen and being presented, ie., whether an HLA-A2 restricted tumor antigen peptide originated from SART-1 is present.

DISCLOSURE OF INVENTION

The purpose or the preftnt invention to to provide HLA-A2 restricted tumor antigen peptides of SART-1 origin. Thus, the present invention provides an HLA-A2 restricted tumor antigen peptide originated from SART-1, a derivative thereof having characteristics functionally equivalent thereto, compositions for treating, preventing or diagnosing tumors which make use of the tumor antigen peptide or its derivative in vivo or in vitro. The SART-1-originated HLA-A2 restricted tumor antigen peptides of the present invention are presented when bound to HLA-A2 which about 40% population of Japanese or Caucasian possesses. Accordingly, the tumor antigen peptides of the present invention are useful in the treatment of a large number of patients and expected to be useful as novel anti-tumor agents since they are applicable to squamous cell carcinoma that shows the highest incidence among human cancers. In this connection, esophageal cancer and lung cancer, among squamous cell carcinomas, are known to be relatively resistant to current chemotherapy or radiotherapy. From this viewpoint, the development of the tumor antigen peptides of the present invention was highly demanded.

The present inventors made intensive investigations to elucidate whether an HLA-A2 restricted tumor antigen peptide is contained in SART-1 molecule as will be hereinafter described.

Thus, the present inventors first established an HLA-A2 restricted CTL cell line from tumor invasive lymphocytes (TIL) derived from a specimen surgically obtained from esophageal cancer, which belong to squamous cell carcinomas when classified on the basis of the tissue type, and named YK-EC (Deposition No. FERM BP-6726). The YK-EC was found to be activated to produce IFN-γ when it was reacted with VA-13 cells that had been doubly transfected with recombinant plasmids each containing SART-1 cDNA and HLA-A0201 cDNA. As a result, it was proved for the first time that SART-1 comprises HLA-A2 restricted tumor antigen peptides.

The present inventors then tried to identify SART-1-originated partial peptides capable of binding to HLA-A2 and being presented, and found that peptides having amino acid sequences as set forth in SEQ ID NO: 1 to SEQ ID NO: 6 or the like possess an activity as tumor antigen peptides. The present invention has been established on the basis of the findings above.

Thus, the present invention is related to:

(1) A tumor antigen peptide which is a partial peptide of SART-1 origin and capable of binding to HLA-A2 antigen and being recognized by cytotoxic T lymphocytes, or a derivative thereof having characteristics functionally equivalent thereto;

(2) The tumor antigen peptide described in (1) above, which has an amino acid sequence selected from those each comprising the entire or a partial amino acid sequence(s) of that shown in any one of SEQ ID NO: 1 to SEQ ID NO: 34, or a derivative thereof having characteristics functionally equivalent thereto;

(3) The tumor antigen peptide described in (2) above, which has an amino acid sequence selected from those each comprising the entire or a partial amino acid sequence(s) of that shown in any one of SEQ ID NO: 1 to SEQ ID NO: 6, or a derivative thereof having characteristics functionally equivalent thereto;

(4) The tumor antigen peptide derivative described in (2) above, which has an amino acid sequence selected from those each comprising the entire or a partial amino acid sequence(s) of a sequence wherein the amino acid residue at position 2 and/or C-terminus of the sequence shown in any one of SEQ ID NO: 1 to SEQ ID NO: 34 is replaced by different one;

(5) The tumor antigen peptide derivative described in (4) above, which has an amino acid sequence selected from those each comprising the entire or a partial amino acid sequence(s) of a sequence wherein the amino acid residue at position 2 and/or C-terminus of the sequence shown in any one of SEQ ID NO: 1 to SEQ ID NO: 6 is replaced by different one;

(6) The tumor antigen peptide derivative described in (4) above, which has an amino acid sequence selected from those each comprising the entire or a partial amino acid sequence(s) of a sequence wherein, in the sequence shown in any one of SEQ ID NO: 1 to SEQ ID NO: 34, the amino acid residue at position 2 is replaced by leucine, methionine, valine, isoleucine or glutamine and/or the C-terminal amino acid residue replaced by valine or leucine;

(7) The tumor antigen peptide derivative described in (6) above, which has an amino acid sequence selected from those comprising the entire or a partial amino acid sequence(s) of that shown in any one of SEQ ID NO: 35 to SEQ ID NO: 40;

(8) A therapeutic or prophylactic agent for tumors, which comprises at least one substance selected from the tumor antigen peptides and derivatives thereof described in any one of (1) to (7) above as an active ingredient;

(9) A recombinant DNA, which comprises at least one DNA encoding a tumor antigen peptide or a derivative thereof described in any one of (1) to (7) above;

(10) A polypeptide obtainable by allowing to express the recombinant DNA described in (9) above;

(11) A therapeutic or prophylactic agent for tumors comprising a recombinant DNA or a polypeptide described in (9) or (10) above as an active ingredient;

(12) A diagnostic agent for tumors comprising a tumor antigen peptide or a derivative thereof described in any one of (1) to (7) above or a polypeptide described in (10) above;

(13) An antibody capable of specifically binding to a tumor antigen peptide or a derivative thereof as described in any one of (1) to (7) above;

(14) An antigen-presenting cell (hereinafter, "APC") presenting a complex between an HLA-A2 antigen and a tumor antigen peptide or its derivative as described in any one of (1) to (7) above on the surface of a cell having an ability to present an antigen and being isolated from a tumor patient;

(15). The APC of (14) above which is obtainable by allowing a cell having an ability to present an antigen and being isolated from a tumor patient to uptake the recombinant DNA or a polypeptide described in (9) or (10) above;

(16) A therapeutic agent for tumor comprising the APC described in (14) or (15) above as an active ingredient;

(17) A cytotoxic T lymphocyte (hereinafter, "CTL") which recognizes specifically a complex between an HLA-A2 antigen and a tumor antigen peptide or a derivative thereof described in any one of (1) to (7) above;

(18) A therapeutic agent for tumor comprising the CTL described in (17) above as an active ingredient;

(19) The CTL described in (17) above which is YK-EC (Deposition No. FERM BP-6726); and

(20) A process for identifying a tumor antigen protein or a tumor antigen peptide characterized in that it uses YK-EC described in (19) above.

BEST MODE FOR CARRYING OUT THE INVENTION

In connection with the present invention, the term "tumor antigen peptide" herein used refers to a partial peptide which is originated from a tumor antigen protein named SART-1 (*J. E. Med.*, 187: 277, 1998, WO97/46676) and can be recognized by CTL when bound to HLA-A2 antigen. Accordingly, any peptide fragments having a partial amino acid sequence of SART-1 shown in SEQ ID NO: 1 of WO97/46676 and being able to form a complex with HLA-A2 antigen, which complex can be recognized by CTL, fall within the scope of the tumor antigen peptides of the present invention irrespective of the length or the original position in the amino acid sequence of SART-1. The tumor antigen peptides of the present invention can be identified by synthesizing a candidate peptide, which is a partial fragment of SART-1, and determining whether or not CTL recognizes a complex between said peptide and HLA-A2 antigen, that is, the candidate peptide has activity as a tumor antigen peptide, according to a method herein provided or any methods available to one ordinary skilled in the art.

Peptides can be synthesized according to processes generally used in the field of peptide chemistry. Such methods can be found in literatures, for example, *Peptide Synthesis,*

Interscience, New York, 1966; *The Proteins*, Vol. 2, Academic Press Inc., New York, 1976; *Peptide Synthesis, Maruzen, Inc.*, 1975; *Peptide-Gosei no Kiso to Jikken, Maruzen, Inc.*, 1985; *Iyakuhin no Kaihatsu* (Zoku), Vol. 14, Peptide Synthesis, *Hirokawa-syoten*, 1991.

The phrase "capable of binding to HLA-A2 antigen and being recognized by CTL" herein used in connection with the present invention means that the tumor antigen peptide of the present invention can bind to HLA-A2 antigen to form a complex which is recognized by CTL.

One can examine whether such a candidate peptide as mentioned above is able to bind to HLA-A2 antigen and be recognized by CTL, that is, whether the said peptide has activity as an HLA-A2-restricted tumor antigen peptide, by a method described in, for example, *J. Inmunol.*, 154, p2257, 1995. Specifically, peripheral blood lymphocytes are isolated from an HLA-A2 antigen-positive human and stimulated in vitro by adding a candidate peptide; and it is determined whether or not CTLs that specifically recognize HLA-A2-positive cells pulsed with the said peptide are induced. The determination whether CTL has been induced can be effected by, for example, measuring the amounts of various cytokines (for example, IFN-γ) produced by CTL in response to the APCs (target cells) using an enzyme-linked immunosorbent assay (ELISA) or the like. APCs (target cells) used in the method include T2 cells which are HLA-A2-positive but unable to present endogenous peptides (*Immungenetics*, 21: 235, 1985) or cells obtained by introducing an expression plasmid containing HLA-A2 cDNA (Genbank Accession No.M84379) into COS-7 cells (ATCC No. CRL1651) or VA-13 cells (RIKEN CELL BANK, The Institute of Physical and Chemical Research), which cells were pulsed with the above candidate peptide. It can also be examined by a method wherein the cytotoxicity of CTL against APCs (target cells) labeled with $^{51}$Cr is measured ($^{51}$Cr release assay, *Int. J. Cancer*, 58:317, 1994).

Alternatively, the examination can also be done by pulsing T2 cells which are HLA-A2-positive but unable to present endogenous peptides (*Immunogenetics*, 21: 235, 1985), or COS-7 cells (ATCC No. CRL1651) or VA=13 cells (RIKEN CELL BANK) to which an expression plasmid containing HLA-A2 cDNA (Genbank Accession No.M84379) has been introduced with the above-mentioned candidate peptide, subjecting the pulsed cells to reaction with YK-EC (Deposit Number: FERM BP-6726) which is an HLA-A2-restricted CTL cell line established by the present invention or other CTLs prepared as mentioned above, and measuring the amounts of various cytolines (for example, IFN-γ) produced by the said CTLs (*J. Em. Med.*, 187:277, 1998).

The methods for determination above may be referred to as "measurement of tumor antigen peptide".

There are certain rules (motifs) in the sequences of antigen peptides capable of binding to HLA molecules and being presented. Concerning the motif for HLA-A2, the following motifs shown in Table 1 are known (*Immunogenetics*, 41:178, 1995; *J. Immunol.*, 155: 4749–4756, 1995).

TABLE 1

Motif of HLA-A2-restricted Antigen Peptides*

| HLA-A2 type | 2nd amino acid from the N-terminus | Amino acid at C-terminus |
|---|---|---|
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

*The length of peptides is 8–11 amino acids.

Accordingly, the HLA-A2-restilcted tumor antigen peptides of the present invention can be selected by synthesizing partial peptides having a motif structure listed above in the amino acid sequence of SART-1 using the above-mentioned process for peptide synthesis, and subjecting the resultant peptides to the "measurement of tumnor antigen peptide" above.

Thus, examples of tumor antigen peptide of the present invention include tumor antigen peptides, which are related to the above-mentioned motif structure on the amino acid sequence of SART-1, and able to bind to HLA-A2 antigen and thereby recognized by CTL. Specific examples include tumor antigen peptides which have an amino acid sequence selected from those each comprising the entire or a partial amino acid sequence(s) of the sequence described in any one of SEQ ID NO: 1 to SEQ ID NO: 34, and are able to bind to HLA-A2 antigen and recognized by CTL. Considering that the peptides are bound to HLA-A2 antigen and presented, they may be about 8to 11 amino acid in length.

The phrase herein used "tumor antigen peptides which have an amino acid sequence selected from those each comprising the entire or a partial amino acid sequences) of the sequence described in any one of SEQ ID NO: 1 to SEQ ID NO: 34, and are able to bind to HLA-A2 antigen and recognzd by CTL" refers to the following peptides.

1) A peptide consisting of an amino acid sequence shown in any one of SEQ ID NO: 1 to SEQ ID NO: 34 or a contiguous partial amino acid sequence thereof; or
2) A peptide comprising the peptide described in 1) above, wherein the peptide can bind to HLA-A2 antigen and be recognized by CTL.

As to the length of the peptide of 1) or 2) above, it would be between 8 and 11 amino acid long. Examples of peptides of 2) above include those having an amino acid sequence wherein an additional amino acid(s) is attached to N- and/or C-termiinus of the entire or a partial amino acid sequence shown in any one of SEQ ID NO: 1–34, which partial amino acid sequence lacks N- and/or C-terminal amino acid(s), and being capable of binding to HLA-A2 and recognized by CTL.

Examples of preferred tumor antigen peptides among others include those comprising the entire or a partial amino acid sequence of an amino acid sequence described in any one of SEQ ID NO: 1 to SEQ ID NO: 20 and is capable of binding to HLA-A2 antigen and recognized by CTL. The phrase herein used, i.e., "tumor antigen peptides comprising the entire or a partial amino acid sequence of a given amino acid sequence and is capable of binding to HLA-A2 antigen and recognized by CTL" means that the said peptides are similar to those described in 1) and 2) above.

Specific examples include tumor antigen peptides comprising the entire or a partial amino acid sequence described in any one of SEQ ID NO: 1 to SEQ ID NO: 6 and capable of being able to bind to HLA-A2 antigen and recognized by CTL. The expression herein used, i.e., "tumor antigen peptides comprising the entire or a partial amino acid sequence of a given amino acid sequence and is capable of binding to HLA-A2 antigen and recognized by CTL" means that the said peptides are similar to those described in 1) and 2) above.

The phrase "a derivative (of tumor antigen peptide) having characteristics functionally equivalent to the tumor antigen peptide", which may be hereinafter referred to as "tumor antigen peptide derivative", refers to a variant which has an amino acid sequence wherein one to several amino acid residues are changed in the amino acid sequence of a tumor antigen peptide of the present invention and yet has the characteristics as a tumor antigen peptide, i.e., it can be recognized by CTL when bound to HLA-A2 antigen, Accordingly, any variants having one to several amino acid changes in the amino acid sequence of tumor antigen peptide of the present invention fall within the scope of the tumor antigen peptide derivative of the present invention as far as they have the activity as a tumor antigen peptide whereby they can bind to HLA-A2 antigen and be recognized by CTL.

The term "change" of amino acid residue means the substitution, deleton and/or addition of amino acid residue (s), wherein the "addition" includes the addition of amino acid(s) at N- and/or C-terminus of a peptide, and amino acid substitution is preferred. In case of substitution, the number or position of amino acid to be chan ged is not restricted on condition that the activity as the tumor antigen peptide is maintained. The preferred length of the tumor antigen peptide derivative of the present invention is, similar to the above-mentioned tumor antigen peptide, about 8 to 11 amino acids.

As mentioned above, there are certain rules (motifs) in the amino acid sequence of antigen peptide presented as a complex with an HLA antigen, and in case of HLA-A2 antigen, the motifs shown in Table 1 are known (*Immunogenetics*, 41:178, 1995, J. Immunol., 155: 4749–4756, 1995). Further, amino acid residues which share a similar property with an amino acid(s) which can be contained in the motif would be allowable too. Accordingly, examples of tumor antigen peptide derivative of the present invention include those comprising the entire or a part of an amino acid sequence wherein a replaceable amino acid residue(s) at, for instance, position 2 and/or C-terminus, of the amino acid sequence shown in any one of SEQ ID NO: 1 to SEQ ID NO: 34, preferably, SEQ ID NO: 1 to SEQ ID NO: 20, is replaced by other amino acid(s), taking the motif above into consideration. Examples of preferred tumor antigen peptide derivatives include those comprising the entire or a part of an amino acid sequence wherein a replaceable amino acid residue(s) at position 2 and/or C-terminus is replaced by other allowable amino acid residue(s) in view of the motif above, more specifically, an amino acid sequence wherein the amino acid residue at position 2 is replaced by leucine, methionine, valine, isoleucine or glutamine and/or the C-terminal amino acid residue replaced by valine or leucine, in the amino acid sequence shown in any one of SEQ ID NO: 1 to SEQ ID NO: 34, preferably, SEQ ID NO: 1 to SEQ ID NO: 20. The length of the peptide is preferably between 8 and 11 amino acids so that it bounds to HLA-A2 and presented.

Examples of such tumor peptide derivatives include those comprising the entire or a part of an amino acid sequence wherein the amino acid residue at position 2 and/or C-terminus is replaced by other amino acid residue(s), preferably, the amino acid residue at position 2 is replaced by leucine, methionine, valine, isoleucine or glutamine and/or the C-terminal residue replaced by valine or leucine, in the amino acid sequence shown in any one of SEQ ID NO: 1 to SEQ ID NO: 6. These illustrative variant peptides are shown in SEQ ID NO: 35 to SEQ ID NO: 40, respectively.

The tumor antigen peptide derivatives of the present invention can be obtained by, just like the tumor antigen peptide of the present invention, synthesizing a candidate peptide according to the method for peptide synthesis, and subjecting the resultant peptide to the above-mentioned measurement of tumor antigen peptide to determine whether or not it has functional characteristics equivalent to tumor antigen peptides.

The tumor antigen peptide or a derivative thereof of the present invention is useful as a prophylactic or therapeutic agent for tumors, wherein at least one tumor antigen peptide or a derivative thereof is used. Thus, the present invention provides a therapeutic or prophylactic agent for tumors that comprises as an active ingredient at least one of the above-described tumor antigen peptide or a derivative thereof. When a therapeutic or prophylactic agent for tumors of the present invention is administered to a patient who is HLA-A2-positive and SART-1-positive, the said peptide or a derivative thereof forms a complex with an HLA-A2 antigen molecule present on the cell surface of APCs directly or is uptaken by APCs and intracellurarly forms an HLA-A2 antigen complex which is transferred to the cell surface, the resultant complex is presented on the cell surface of APCs at high density, and CTLs specific for the presented complex proliferate and destroy the tumor cells. The treatment or prevention of tumor is thus achieved.

The SART-1 being widely expressed on squamous cell carcinomas such as esophageal cancer, lung cancer, and the like, the therapeutic or prophylactic agent for tumors of the present invention has an advantage of showing a wide range of applicability. Furthermore, although the above squamous cell carcinomas often exhibit resistance to chemotherapy and radiotherapy, the therapeutic effect of chemotherapy and radiotherapy can be enhanced by using the therapeutic agent for tumors of the present invention as a combined therapy.

A therapeutic or prophylactic agent for tumors of the present invention may be administered along with an adjuvant, or may be administered in a particulate dosage form In order to effectively establish the cellular immunity. For such purpose, those adjuvants described in the literature (*Clin. Microbiol. Rev.*, 7:277–289, 1994) are usable. In addition, liposomal preparations, particulate preparations in which the peptides are bound to beads having a diameter of several $\mu$m, or preparations in which the peptides are attached to lipids, are also usable. Administration may be achieved, for example, intradermally, hypodermically, by intravenous injection, or the like. Although the dose of a tumor antigen peptide or a derivative thereof of the present invention may be adjusted as appropriate depending on, for example, the disease to be treated, the age and the body weight of a particular patient, it would be usually from 0.0001 mg to 1000 mg, preferably 0.001 mg to 100 mg, and more preferably 0.01 mg to 10 mg of the peptide every several days to every several months.

The therapeutic or prophylactic agent of the present invention may contain, as an active ingredient, not only the tumor antigen peptide or its derivative of the present invention but also DNA encoding the tumor antigen peptide or its derivative, or a polypeptide as an expression product of said DNA of the present invention.

Thus, there has recently been developed a vaccination method which uses a DNA encoding "polytope" wherein plural of CTL-epitopes are ligated as a DNA vaccine. See, for example, *Journal of Immunology*, 160, p1717, 1998 etc. Thus, when used as an active ingredient of a therapeutic or a prophylactic agent, one or more DNAs encoding a tumor antigen peptide or a derivative thereof of the present invention and, if desired, a DNA(s) encoding other tumor antigen peptide are ligated to obtain a recombinant DNA which is then inserted into an appropriate expression vector. Similar to the recombinant DNA above, a polypeptide obtained by expressing the said recombinant DNA in host cells is also useful as an active ingredient of a therapeutic or prophylactic agent for tumors.

The "recombinant DNA" can be made easily by any methods for the synthesis of DNA or ordinary gene technological procedures in accordance with the teaching of basic texts such as Molecular Cloning 2nd Ed., Cold Spring Harbor Laboratory Press (1989). The insertion of the recombinant DNA into an expression vector can also be carried out according to the teaching of the above-mentioned basis text.

It can be determined whether the resultant recombinant DNA of the present invention may give a tumor antigen peptide that is recognized by CTL after binding with HLA-A2 antigen, for example, by the following method.

Firstly, an expression plasmid containing a recombinant DNA and another expression plasmid containing cDNA encoding HLA-A2 antigen (Genbank Accession No. M84379) are doubly transfected into cells such as COS-7 (ATCC CRL 1651) or fibroblast VA-13 (RIKEN CELL BANK, The Institute of Physical and Chemical Research). The transfection may be achieved, for example, by Lipofectin method using Lipofectamine reagent (GIBCO BRL). Subsequently, HLA-A2-restncted CTL (e.g., YK-EC, FERM BP-6726) is added to the transfectants for reaction, and the amount of various cytokines (for example, IFN-γ) produced by said CTL in response is measured by, for example, ELISA to determine whether the candidate DNA has the activity.

When applying the recombinant DNA of the present invention to the therapeutic or prophylactic agent for tumor, the following methods are usable.

Thus, examples of a method of introducing the recombinant DNA of the present invention into cells include a method which employs viral vectors and those described in literatures (*Nikkei-Sience*, April, 1994, pp. 20–45; *Gekkan-Yakuji*, 36(1), 23–48 (1994); *Jikken-Igak-Zokan*, 12(15), 1994, and references cited therein), and any one of such methods may be applied to the present invention.

Examples of methods which use viral vectors include those wherein the DNA of the present invention is incorporated into DNA or RNA virus such as retrovirus, adenovirus, adeno-associated virus, herpesvirus, vaccinia virus, poxvirus, poliovirus, or Sindbis virus, and then introduced into cells. Among them, the methods using retrovirus, adenovirus, adeno-associated virus, or vaccinia virus are particularly preferred.

Further, there is another method wherein expression plasmids are directly injected intramuscularly (DNA vaccination), the liposome method, Lipofectin method, mrnicmection, the calcium phosphate method, and electroporation. Among them, DNA vaccination and the liposome method are particularly preferred.

In order to make the recombinant DNA of the present invention act as pharmaceutical in practice, one can use either of two methods: in vivo method in which DNA is directly introduced into the body, or ex vivo method in which certain kinds of cells are removed from human, and after introducing DNA into said cells outside of the body, reintroduced into the body (*Nikkei-Science*, April, 1994, pp. 20–45; *Gekkan-Yakuji*, 36(1), 23–48 (1994); *fikkenn-Igaku-Zokan*, 12(15), 1994; and references cited therein). In vivo method is more preferable.

In the case of in uiwo methods, a DNA of the present invention may be administered via any appropriate route depending on the diseases and symptoms to be treated, and other factors. For example, it may be administered via intravenous, intraarterial, subcutaneous, intracutaneous, or intramuscular routes. In the case of in vivo methods, such pharmaceuticals may be administered in various dosage forms such as solution, and they are typically formulated into injections containing a recombinant DNA of the present invention as an active ingredient, which may also include, as needed, conventional carriers. When a recombinant DNA of the present invention is included in liposomes or membrane-fused liposomes (such as Sendai virus (HVJ)-liposomes), such medicines may be in the form of suspension, frozen drug, centrifugally-concentrated frozen drug or the like.

Although the amount of a recombinant DNA of the present invention in such formulations varies depending on, for example, the disease to be treated, the age and body weight of a particular patient, it is usually preferred to administer 0.0001–100 mg, more preferably 0.001–10 mg, of a recombinant DNA of the present invention at every several days to every several months.

When a recombinant DNA of the present invention as described above is administered to a patient, polypeptides corresponding to the said recombinant DNA are expressed to a high extent and intracellularly processed, the resultant tumor antigen peptide frament forms a complex with an HLA antigen and presented on the cell surface of APC at high density, CTLs specific for the complex proliferate efficiently in vivo, and tumor cells are destroyed thereby. The treatment or prevention of tumor would be achieved in this manner.

The "recombinant polypeptide" which may be referred to as simply "polypeptide" as the expression product of the above-mentioned recombinant DNA can be prepared by transforming appropriate host cells with an expression plasmid constructed by inserting a recombinant DNA above to an appropriate expression vector (e.g., pSV-SPORT1) and culturing the transformants in an appropriate medium. Examples of host cell include prokaryotes such as *Eschenclia coli*, unicellular eukaryotes such as yeast, and cells derived from multicellular eukaryotes such as insects or animals. Transformation of host cells with an expression plasmid can be carried out by a known method such as the calcium phosphate method, DEAE-dextran method, or the electric pulse method. The polypeptide thus obtained can be isolated and purified according to standard biochemical procedures. The determination whether the said polypeptide gives a tumor antigen peptide(s) capable of being recognized by CTL after binding to HLA-A2 can be carried out, for example, by allowing phagocytes such as macrophages uptake the polypeptides of the present invention to produce peptide fragments intracellarly, reacting the complex formed between the resultant peptide fragment and HLA-A2 antigen with CTL such as YK-EC (FERM BP6726), and measuring the amount of various cytolines (for example, IFN-γ) produced by said CTL in response.

When using the polypeptide of the present invention as a therapeutic or prophylactic agent for tumors, the dosage form, administration method and dose are the same as that mentioned above in connection with the tumor antigen peptide or a derivative thereof of the present invention. When the polypeptide of the present invention is administered to a tumor patient, it is uptaken by APC, the resultant tumor antigen peptide produced by intracellular processing forms a complex with an HLA antigen and presented on the cell surface of APC at high density, and CTLs specific for the said complex efficiently proliferate in vivo and destroy tumor cells. In this manner, the treatment and prophylaxis of tumors would be achieved.

The present invention provides an antibody that specifically binds to a tumor antigen peptide or a derivative thereof of the present invention. Such antibodies are easily prepared, for example, according to the method described in "Antibodies: A Laboratory Manual", Lane, H. D. et al. eds., Cold Spring Harbor Laboratory Press, New York, 1989. Specifically, antibodies having an ability to recognize and, further, to neutralize the activity of a tumor antigen peptide or its derivative can be made easily by immunizing an animal with a tumor antigen peptide or its derivative of the present invention in a conventional manner. Examples of the field of application of such antibodies include affinity chromatography, immunological diagnosis, and the like. For the immunological diagnosis, an appropriate method can be selected from immunoblotting, radioimmunoassay (RIA), enzme-liflcd immunosorbent assay (ELISA), and a fluorescent or luminescent assay.

A polypeptide or its derivative of the present invention, or a recombinant DNA of the present invention or a polypeptide obtainable by allowing to express the recombinant DNA are usable in vitro in the treatment of tumor patients in the following manner.

That is, when using a tumor antigen peptide or its derivative in the treatment of tumor patient, it is significant to establish an administration method which allows an efficient in vivo induction of specific CTLs. As one measure for this purpose, the present invention provides an APC comprising a complex between HLA-A2 antigen and a tumor antigen peptide or its derivative, the complex being presented on the surface of an isolated cell which has an antigen-presenting ability and is derived from a tumor patient, or a therapeutic agent for tumor containing the said APC as an active ingredient.

The term "cell having an antigen-presenting ability" is not specifically restricted to any cell so long as it expresses an HLA-A2 antigen capable of presenting a tumor antigen or its derivative of the present invention on the surface. Dendritic cells, which are reported to have an especially high antigen-presenting ability, are preferred.

Substances to be added for preparing the APCs of the present invention from cells having an antigen-presenting ability include not only a tumor antigen peptide or a derivative thereof of the present invention but also a recombinant DNA or a polypeptide of the present invention.

In order to prepare such APCs of the present invention, cells having an antigen-presenting ability are isolated from a tumor patient, and pulsed ex vivo with a tumor antigen peptide or its derivative of the present invention, or a polypeptide of the present invention to form a complex between HLA-A2 antigen and the peptide or its derivative above (*Cancer Immunol, Immunother.*, 46;82, 1998; *J.Immunol.*, 158: p1796, 1997; *Cancer Res.*, 59: p1184, 1999). In case that dendritic cells are used, the APC of the present invention can be prepared as follows. Lymphocytes are isolated from peripheral blood of a tumor patient by Ficoll method; adherent cells are separated from non-adherent cells; the adherent cells are then cultured in the presence of GM-CSF and IL-4 to induce dendritic cells; and the dendritic cells are pulsed by culturing with a tumor antigen peptide or a polypeptide of the present invention to obtain the APCs of the present invention.

When the APC of the present invention is prepared by introducing a recombinant DNA of the present invention into the above-mentioned cells having antigen-presenting ability, it can be carried out in accordance with the teaching in *Cancer Res.*, 56: p5672, 1996 or *J. Immunol.*, 161: p5607, 1998, and the like. Further, RNA, as well as DNA, is usable for the preparation of APC in accordance with the teaching of *J. E. Med*, 184: p465, 1996, and the like.

A therapeutic agent for tumors that comprises the above APCs as an active ingredient preferably contains physiological saline, phosphate buffered saline (PBS), culture medium, or the like in order to stably maintain the APCS. Administration may be achieved, for example, intravenously, hypodermically, or intradermaluy. By returning the above therapeutic agent for tumors into the patient's body, specific CTL is efficiently induced in the patient who is HLA-A2 positive and also positive for SART-1, and thereby tumor can be treated.

In addition, another example of in vitro use of tumor antigen peptide or its derivative of the present invention may be in the following adoptive immunotherapy.

In the case of melannoma, it has been observed that an adoptive immunotherapy wherein intratumoral T cell infiltrate taken from the patient himself/herself are cultured ex vivo in large quantities, and then returned into the patient achieves a therapeutic gain (*J. Natl. Cancer. Inst.*, 86:1159, 1994). Furthermore, in mouse melanoma, suppression of metastasis has been observed by stimulating splenocytes in vitro with a tumor antigen peptide TRP-2, thereby proliferating CTLs specific for the tumor antigen peptide, and then administering said CTLs into a mouse carrying grafted melanoma (*J. Exp. Med.*, 185:453, 1997). This resulted from in vitro proliferation of CTL that specifically recognizes the complex between an HLA antigen of APCs and the tumor antigen peptide. Accordingly, a method for treating tumors which comprises stimulating in vitro peripheral blood lymphocytes of a patient with a tumor antigen peptide, a derivative thereof, a recombinant DNA or a polypeptide of the present invention to make tumor-specific CTLs proliferate, and returning the CTLs into the patient is believed to be useful.

Accordingly, the present invention also provides CTLs that specifically recognize a complex between the above-mentioned HLA-A2 antigen and the tumor antigen peptide or its derivative of the present invention and a therapeutic agent for tumors containing the said CTLs as an active ingredient. It is preferred that the therapeutic agent contains physiological saline, phosphate buffered saline (PBS), culture medium, or the like in order to stably maintain CTLs. Administration may be achieved, for example, intravenously, hypodermically, or intradermally. By returning the above therapeutic agent containing CTLs as an active ingredient into the patient's body, the toxicity of CTLs on tumor cells is enhanced in the patient who is HLA-A2 positive and is also positive for SART-1. The tumor cells are destroyed and thereby the treatment of tumor is achieved.

Further, the tumor antigen peptide or a derivative thereof, or a polypeptide of the present invention can be used as an ingredient of an agent for diagnosis of tumors. That is, the tumor antigen peptide or its derivative of the present invention serves as a diagnostic agent which is useful in the detection of an antibody in a sample (such as blood, a tumor tissue, or the like) obtained from a patient suspected to have a tumor. In this manner, one can detect tumors in early-stage, or diagnose recurrent or metastatic tumors. Further, it may be used for screening of tumor patients adaptable to pharmaceuticals containing tumor antigen peptides or the like of the present invention as an active ingredient. Specifically, the diagnosis can be effected using immunoblotting, RIA, ELISA, or fluorescent or luminescent assay.

Furthermore, there have recently been established a new method of detecting antigen-specific CTLs that uses a complex between an antigen peptide and an HLA antigen (*Science*, 274: p94, 1996). A complex of a tumor antigen peptide or its derivative of the present invention and an HLA-A2 antigen may be applied to the said detection method to detect CTLs specific for tumor antigen whereby one can detect tumors in early-phase, or diagnosis recurrence or metastasis of tumor. Further, it can be used for selecting patients adaptable to the pharmaceuticals of the present invention or the therapeutic effect thereof, which pharmaceuticals contain as an active ingredient a tumor antigen peptide of the present invention or the like. Thus, the present invention provides a diagnostic agent for tumors comprising a tumor antigen peptide or its derivative of the present invention.

Specifically, the diagnosis above can be carried out as follows: a tetramer of a complex between tumor antigen peptide and fluorescence-labeled HLA-A2 antigen obtained by a method described in *Science*, 274: p94, 1996 is prepared and subjected to the flowey to metry and the amount of CTLs specific for antigen peptide among peripheral blood lymphocytes derived from a patient suspected to have a tumor is determined.

The present invention also provides YK-EC (Deposition No. FERM BP-6726) which is a CTL cell line established from intratumoral invasive lymphocytes derived from an esophageal tumor. YK-EC has been proved to be a CTL cell line restricted to HLA-A2. The tumor antigen peptide of the present invention, which is restricted to HLA-A2, has been found on the basis of the reactivity with YK-EC as an index. Accordingly, it is possible to further identify tumor antigen proteins and HLA-A2 restricted tumor antigen peptides which are novel by means of YK-EC. The present invention also encompasses such methods. The method can be effected, for example, in a manner similar to that described generally in "measurement of tumor antigen peptide" above, and specifically in Examples 2 and 4 below.

The following Examples are provided to further illustrate the present invention and are not to be construed as limiting the scope thereof.

Example 1

Establishment of Cytotoxic T Lymphocyte (CTL) Cell Line from Intratumoral Invasive Lymphocytes (TIL) of Esophageal Cancer Origin According to the disclosure of Seid et al., *Cell Immunol.* 175: 101–110 (1997), HLA-A2-restricted CTL cell line was established from a TIL obtained from a surgical specimen of esophageal cancer belonging to squamous cell carcinomas when claifed on the basis of the tissue type, named YK-EC and used in the following experiments. YK-EC has been deposited at "The National Institute of Bioscience and Human Technology", 1-1-3 Higashi, Tsukuba, Ibaraki, Japan (Identification of microorganism: YA-EC; Accession date; Jun. 19, 1998; Deposition No. FERM P-16855), and the deposition was transferred to international one on May 20, 1999 (International Deposition No. FERM BP-6726).

Example 2

Reactivity of YK-EC on Tumor Antigen Protein SART-1

A recombinant plasmid was prepared by incorporating cDNA encoding HLA-A0201 (Genbank Accession No. M84379) from SW620 (ATCC cell line No. CCL-227) into an expression vector pCR3 (INVITROGEN) in accordance with the description by Nakao et al. (*Cancer. Res.*,55: 4248–4252,1995).

Fibroblast cell line, VA-13 cells (RIKEN CELL BANK, The Institute of Physical and Chemical Research; *Ann. Med. Exp. Biol. Fenn.*, 44:242, 1966) were doubly transfected with the recombinant plascid containing HLA-A0201 cDNA and a recombinant plasmnid 6DI containing a cDNA encoding a partial sequence of tumor antigen protein SART-1 (WO97/46676) by Lipofectin method as described in *J. Exp. Med.*, 187: 277, 1998 as follows. In this connection, *E. coli* JM109 (K3) carrying full-length cDNA (SEQ. ID NO: 2 of WO97/46676) encoding SART-1 has been deposited under Deposition No. FERM BP-5951, and plasmid K3 obtainable therefrom can be used instead of 6DI.

Specifically, $10^4$ of VA-13 cells were placed in each well of 96-well microplate, and incubated in RPMI 1640 medium containing 10% FCS. VA-13 cells were doubly transfected with 30 μl mixture consisting of 100 ng of the recombinant plasmid for HLA-A0201 cDNA and 100 ng of 6DI by using Lipofectin reagent (GIBCO BRL). Transfectants were prepared in duplicate. After 5-hour-incubation, 200 μl of culture medium was added to the transfectants, and the incubation continued for 72 hours. The culture medium was removed and $2 \times 10^4$ YK-EC were added, which was followed by cultivation for 18 to 24 hours. The culture medium was recovered, and the amount of IFN-γ was measured by ELISA. Specifically, an anti-humnan IFN-γ mouse monoclonal antibody was allowed to adsorb on wells of 96-well microplate to provide a solid-phased antibody. After blocking non-specific bindings with bovine serum albumin, the solid-phased antibody was allowed to bind with IFN-γ in the test sample. Anti-human IFN-γ rabbit polyclonal antibody as a detection antibody was then allowed to bind, which was followed by binding with an anti-rabbit immunoglobulin goat antibody (Amersham) labeled with alkaline phosphatase. The plate was subjected to color development reaction with peroxdase color development kit T (Sumitomo Bakelite), and measurement of absorbance at 405 nm. The absorbance was compared with that obtained with standard IFN-γ to determine the amount of IFN-γ. In the control experiments, the following three groups of cells were treated in the same manner: cells without transfection (non-treated group); cells transfected with recombinant plasmid 6DI alone; and cells transfected with solely recombinant plasmid containing HLA-A201 cDNA. The results are shown in Table 2 below.

TABLE 2

Amount of IFN-γ Produced by YK-EC

| Target cell | Amount of IFN-γ produced by YK-EC (pg/ml) |
| --- | --- |
| VA-13 | 0 |
| VA-13 + HLA-A0201 | 12.2 |
| VA-13 + 6DI | 22.1 |
| VA-13 + HLA-A0201 + 6DI | 94.1 |

When YK-EC was doubly transfected with a recombinant plasmid 6DI containing cDNA encoding a partial sequence of tumor antigen protein SART-1 and a recombinant piasmnid containing cDNA encoding HLA-A0201, the cells responded stronger and produced IFN-γ compared to other groups. These results indicated that a tumor antigen peptide of tumor antigen protein SART-1 is presented to HLA- A0201 and that YK-EC recognized the said tumor antigen peptide; i.e., SART-1 comprises an HLA-A2-restricted tumor antigen peptide(s).

Example 3

Selection and Synthesis of Tumor Antigen Peptide

There are certain rules (motifs) in the sequences of antigen peptides which bind to and presented by HLA molecules. Concerning the HLA-A2, the motifs shown in Table 3 are known (*Immunogenetcs*, 41: 178, 1995; *J. Immunol.*, 155:4749–4756, 1995).

TABLE 3

Motif of HLA-A2-restricted Antigen Peptides*

| HLA-A2 type | 2nd amino acid from the N-terminus | Amino acid at C-terminus |
| --- | --- | --- |
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

*The length of peptides is 8–11 amino acids.

The amino acid sequences of peptides consisting of 9–10 amino acids, each comprising any one of the above-identified motifs which are contained in the tumor antigen protein SART-1 set forth in SEQ ID NO: 1 of WO 97/46676 are shown in SEQ ID NO: 1 to SEQ ID NO: 34. The peptides, each having the amino acid sequence corresponding to the sequence at position 642-650, 642-651, 650-658, 660-668, 712-720 and 778-786 on the amino acid sequence of SART-1 were named "642-650" (SEQ ID NO: 1), "642-651" (SEQ ID NO: 2), "650-658" (SEQ ID NO: 3), "660-668" ((SEQ ID NO: 4), "712-720" (SEQ ID NO: 5), "778-786" (SEQ ID NO: 6), respectively, and synthesized by the solid phase method as follows.

[1] Synthesis of SART-1 "642-650" Leu-Leu-Leu-Cys-Gln-Asn-Lys-Gly-Leu (SEQ ID NO: 1)

Fmoc-Leu-Alko Resin (0.57 mmol/g, 100–200 mesh, Watanabe Kagaku) was used as the resin. The synthesis was initiated using 100 mg of the resin by coupling Fmoc-Gly-OH, Fmoc-Lys(Boc)-OH, Fmoc-Asn-OH, Fmoc-Gln-OH, Fmoc-Cys(tBu)-OH, Fmoc-Leu-OH, Fmoc-Leu-OH and Fmnoc-Leu-OH in sequence according to the Schedule 1 below. After the completion of coupling, the procedures were carried out upto Step 3 of Schedule 1 to obtain the peptide resin.

To the peptide resin was added 2 ml of Reagent K (5% phenol, 5% thioanisole, 5% H2O, 2.5% ethanedithiol/TFA), and the mixture was reacted at room temperature for 2.5 hours. To the reaction solution was added 10 ml of diethyl ether under ice-coolihg. The reaction mixture was stirred for 10 minutes, filtered and washed with 10 ml of diethyl ether. The filter cake was combined with 10 ml of aqueous acetic acid, stirred for 30 minutes and filtered to separate the resin. The resin was washed with 4 ml of aqueous acetic acid. The filtrate and washings were lyophilized, and the resultant crude peptide was dissolved in aqueous acetic acid and loaded onto a reverse phase packing material YMC-PACK ODS-A column (30f×250 nm) pre-equilibrated with 0.1% aqueous TFA. The column was washed with 0.1% aqueous TFA and eluted while increasing the acetonitrile concentration upto 30% over 180 minutes at a flow rate of 7 ml/min. The eluent was monitored at A220 nm and fractions containing the intended substance were collected, lyophilized to obtain 46.3 mg of Leu-Leu-Leu-Cys-Gln-Asn-Lys-Gly-Leu (SEQ ID NO: 1).

The resultant peptide showed retention time of 21.0 minutes when anaryzed by a reverse phase packing material SUMIPACK ODS-A211 column (4.6ϕ×250 nm) eluting with 16 to 46% linear gradient of acetonitrile containing 0.1% TFA. The amino acid analysis (Cys was not detected) and mass spectrometry of the peptide were consistent with the theoretical values.

Amino acid analysis:
Hydrolysis: 1% phenol/6N aqueous hydrochloric acid solution, 110 ° C., 24 hours
Analytical method: ninhydrin method
Asx 0.9 (1)
Gx: 1.0(1)
Gly:0.9(1)
*Leu: 4.0 (4)*reference amino acid
Lys: 1.0 (1)

Theoretical values are indicated in parentheses ( ). Mass spectrometry (FAB) [M+H]$^+$: 1001.6

Schedule 1

| Step | | (min) × times* |
| --- | --- | --- |
| 1. Washing | DMF 1.2 ml | 1 × 2 |
| 2.deprotection | 50% piperidine/DMF | 12 × 1 |
| 3.washing | DMF 1.2 ml | 1 × 7 |
| 4.coupling | An amino-protected amino acid (5 eq.)/ NMP solution 0.9 ml, DIC (5 eq.)/NMP solution 0.3 ml | 30 × 1 |
| 5.washing | DMF 1.2 ml | 1 × 2 |
| 6.coupling | An amino-protected amino acid (5 eq.)/ NMP solution 0.9 ml, DIC (5 eq.)/NMP solution 0.3 ml | 30 × 1 |
| 7.washing | DMF 1.2 ml | 1 × 4 |

*Duration (min) × the number of times of treatment

[2] Synthesis of SART-1 "1642-651" Leu-Leu-Leu-Cys-Gln-Asn-Lys-Gly-Leu-Leu (SEQ ID NO: 2)

Fmoc-Leu-Alko Resin (0.57 mmol/g, 100–200 mesh) was used as the resin. In the same manner as [1] above, Fmoc-Leu-OH, Fmoc-Gly-OH, Fmoc-Lys(Boc)-OH, Fmoc-Asn-OH, Fmoc-Gln-OH, Fmoc-Cys(tBu)-OH, Fmoc-Leu-OH, Fmoc-Leu-OH and Fmoc-Leu-OH were coupled in sequence by using 100 mg resin. After the completion of coupling, the procedures were carried out upto Step 3 of Schedule 1 to obtain the peptide resin.

To the peptide resin was added 2 ml of Reagent K (5% phenol, 5% thioanisole, 5% H2O, 2.5% ethanedithiol/TFA), and the mixture was reacted at room temperature for 2.5 hours. To the reaction solution was added 10 ml of diethyl ether under ice-cooling. The reaction mixture was stirred for 10 minutes, filtered and washed with 10 ml of diethyl ether. The filter cake was combined with 10 ml of aqueous acetic acid, stirred for 30 minutes and filtered to separate the resin. The resin was washed with 4 ml of aqueous acetic acid. The filtrate and washings were lyophilized, and the resultant crude peptide was dissolved in aqueous acetic acid and loaded onto a reverse phase packing material YMC-PACK ODS-A column (30f×250 nm) pre-equilibrated with 0.1% aqueous TFA. The column was washed with 0.1% aqueous TFA and eluted while increasing the acetonitrile concentration upto 32% over 120 minutes at a flow rate of 7 ml/min. The eluent was monitored at A220 nm and fractions containing the intended substance were collected, lyophilized to obtain 27.1 mg of Leu-Leu-Leu-Cys-Gln-Asn-Lys-Gly-Leu-Leu. (SEQ ID NO: 2)

The resultant peptide showed retention time of 22.8 minutes when analyzed by a reverse phase packing material SUMIPACK ODS-A211 column (4.6φ×250 mm) eluting with 18 to 48% linear gradient of acetonitrile containing 0.1% TFA. The amino acid analysis (Cys was not detected) and mass spectrometry were consistent with theoretical values. Amino acid analysis:

Hydrolysis: 1% phenol/6N aqueous hydrochloric acid solution, 110° C., 24 hours

Analytical method: ninhydrin method
  Asx 1.0 (1)
  Glx: 1.0 (1)
  Gly: 0.9 (1)
  *Leu: 5.0 (5)*reference amino acid
  Lys: 0.9 (1)

Theoretical values are indicated in parentheses ( ). Mass spectrometry (FAB) [M+H]$^+$: 1114.6

[3] Synthesis of SART-1 "650-658" Leu-Leu-Glu-Thr-Thr-Val-Gln-Lys-Val (SEQ ID NO: 3)

Fmoc-Val-Alko Resin (0.62 mmol/g, 100–200 mesh) was used as the resin. In the same manner as [1] above, Fmoc-Lys(Boc)-OH, Fmoc-Gln-OH, Fmoc-Val-OH, Fmoc-Thr(tBu)-OH, Fmoc-Thr(tBu)-OH, Fmoc-Glu(OtBu)-OH, Fmoc-Leu-OH, Fmoc-Llu-OH were coupled in sequence by using 100 mg resin. After the completion of coupling, the procedures were carried out upto Step 3 of Schedule 1 to obtain the peptide resin.

To the peptide resin was added 2 ml of Reagent K (5% phenol, 5% thioanisole, 5% H2O, 2.5% ethanedithiol/TFA), and the mixture was reacted at room temperature for 2.5 hours. To the reaction solution was added 10 ml of diethyl ether under ice-cooling. The reaction mixture was stirred for 10 minutes, filtered and washed with 10 ml of diethyl ether. The filter cake was combined with 10 ml of aqueous acetic acid, stirred for 30 minutes and filtered to separate the resin. The resin was washed with 4 ml of aqueous acetic acid. The filtrate and washings were lyophilized, and the resultant crude peptide was dissolved in aqueous acetic acid and loaded onto a reverse phase packing material YMC-PACK ODS-A column (30f×250 nm) pre-equilibrated with 0.1% aqueous TFA. The column was washed with 0.1% aqueous TFA and eluted while increasing the acetonitrile concentration up to 30% over 180 minutes at a flow rate of 7 ml/min. The eluent was monitored at A220 nm and fractions containing the intended substance were collected, lyophilized to obtain 32.2 mg of Leu-Leu-Glu-Thr-Thr-Val-Gln-Lys-Val (SEQ ID NO: 3).

The resultant peptide showed retention time of 20.2 minutes when analyzed by a reverse phase packing material SUMIPACK ODS-A2 11 column (4.6φ×250 nm) eluting with 11 to 41% linear gradient of acetonitrile containing 0.1% TFA. The amino acid analysis and mass spectrometry were consistent with theoretical values.

Amino acid analysis:

Hydrolysis: 1% phenol/6N aqueous hydrochloric acid solution, 110° C., 24 hours

Analytical method: ninhydrin method
  Thr: 1.6 (2)
  Glx: 1.9 (2)
  Val: 1.8 (2)
  *Leu: 2.0 (2)*reference amino acid
  Lys: 0.9 (1)

Theoretical values are indicated in parentheses ( ). Mass spectrometry (FAB) [M +H]$^+$: 1030.6

[4] Synthesis of SART-1 "660-668" Arg-Val-Lys-Ala-Pro-Asn-Lys-Ser-Leu (SEQ ID NO: 4)

Fmoc-Val-Alko Resin (0.57 mmol/g, 100–200 mesh) was used as the resin. In the same manner as [1] above, Fmoc-Ser(tBu)-OH, Fmoc-Lys(Boc)-OH, Fmoc-Asn-OH, Fmoc-Pro-OH, Fmoc-Ala-OH, Fmoc-Lys(Boc)-OH, Fmoc-Val-OH and Fmoc-Arg(Pmc)-OH were coupled in sequence by using 100 mg resin. After the completion of coupling, the procedures were carried out upto Step 3 of Schedule 1 to obtain the peptide resin.

To the peptide resin was added 2 ml of Reagent K (5% phenol, 5% thioanisole, 5% H$_2$O, 2.5% ethanedithiol/TFA), and the mixture was reacted at room temperature for 2.5 hours. To the reaction solution was added 10 ml of diethyl ether under ice-cooling. The reaction mixture was stirred for 10 minutes, filtered and washed with 10 ml of diethyl ether. The filter cake was combined with 10 ml of aqueous acetic acid, stirred for 30 minutes and filtered to separate the resin. The resin was washed with 4 ml of aqueous acetic acid. The filtrate and washings were lyophilized, and the resultant crude peptide was dissolved in aqueous acetic acid and loaded onto a reverse phase packing material YMC-PACK ODS-A column (30φ×250 nm) pre-equilibrated with 0.1% aqueous TFA. The column was washed with 0.1% aqueous TFA and eluted while increasing the acetonitrile concentration upto 20% over 180 minutes at a flow rate of 7 ml/min. The eluent was monitored at A220 nm and fractions containing the intended substance were collected, lyophilized to obtain 44.7 mg of Arg-Val-Lys-Ala-Pro-Asn-Lys-Ser-Leu.

The resultant peptide showed retention time of 20.2 minutes when analyzed by a reverse phase packing material SUMIPACK ODS-A211 column (4.6φ×250 nm) eluting with 6 to 36% linear gradient of acetonitrile containing 0.1% TFA. The amino acid analysis and mass spectrometry were consistent with theoretical values.

Amino acid analysis:

Hydrolysis: 1% phenol/6N aqueous hydrochloric acid solution, 110° C., 24 hours

Analytical method: ninhydrin method
  Asx: 0.9(1)
  Ser: 0.7 (1)
  Ala: 0.9 (1)
  Val: 0.9 (1)
  *Leu: 1.0 (1)*reference amino acid
  Lys: 1.7 (2)
  Arg: 0.8(1)
  Pro: 0.9 (1)

Theoretical values are indicated in parentheses ( ). Mass spectrometry (FAB) [M +H]$^+$: 1012.6

[5] Synthesis of SART-1 "712-720" Tyr-Val-Asp-Glu-Thr-Gly-Arg-Lys-Leu (SEQ ID NO: 5)

Fmoc-Leu-Alko Resin (0.57 mmol/g, 100–200 mesh) was used as the resin. In the same manner as [1] above, Fmoc-Lys(Boc)-OH, Fmoc-Arg(Pmc)-OH, Fmoc-Gly-OH, Fmoc-Thr(tBu)-OH, Fmoc-Glu(OtBu)-OH, Fmoc-Asp(OtBu)-OH, Fmoc-Val-OH and Fmoc-Tyr(tBu)-OH were coupled in sequence by using 100 mg resin. After the completion of coupling, the procedures were carried out upto Step 3 of Schedule 1 to obtain the peptide resin.

To the peptide resin was added 2 ml of Reagent K (5% phenol, 5% thioanisole, 5% H2O, 2.5% ethanedithiol/TFA), and the mixture was reacted at room temperature for 2.5 hours. To the reaction solution was added 10 ml of diethyl ether under ice-cooling. The reaction mixture was stirred for 10 minutes, filtered and washed with 10 ml of diethyl ether. The filter cake was combined with 10 ml of aqueous acetic acid, stirred for 30 minutes and filtered to separate the resin. The resin was washed with 4 ml of aqueous acetic acid. The filtrate and washings were lyophilized, and the resultant crude peptide was dissolved in aqueous acetic acid and loaded onto a reverse phase packing material YMC-PACK ODS-A column (30f×250 nm) pre-equilibrated with 0.1% aqueous TFA. The column was washed with 0.1% aqueous TFA and eluted while increasing the acetonitrile concentration upto 20% over 120 minutes at a flow rate of 7 ml/min. The eluent was monitored at A220 nm and fractions containing the intended substance were collected, lyophilized to obtain 42.3 mg of Tyr-Val-Asp-Glu-Thr-Gly-Arg-Lys-Leu (SEQ ID NO: 5).

The resultant peptide showed retention time of 20.9 minutes when analyzed by a reverse phase packdng material SUMIPACK ODS-A211 column (4.6φ×250 nm) eluting with 7 to 37% linear gradient of acetonitrile containing 0.1% TFA. The amino acid analysis and mass spectrometry were consistent with theoretical values.

Amino acid analysis:
Hydrolysis: 1% phenol/6N aqueous hydrochloric acid solution, 110° C., 24 hours
Analtical method: ninhydrin method
 Asx: 0.9 (1)
 Thr: 0.9 (1)
 Glx: 1.0 (1)
 Gly: 0.9 (1)
 Val: 0.9 (1)
 *Leu: 1.0 (1)*reference amino acid
 Tyr: 1.0 (1)
 Lys: 0.9 (1)
 Arg: 0.9 (1)

Theoretical values are indicated in parentheses ( ). Mass spectrometry (FAB) [M +H]$^+$: 1080.5

[6] Synthesis of SART-1 "778-786" Ala-Gln-Lys-Thr-Pro-Tyr-Ile-Val-Leu (SEQ ID NO: 6)

Fmoc-Leu-Alko Resin (0.57 mmol/g, 100–200 mesh) was used as the resin. In the same manner as [1] above, Fmoc-Val-OH, Fmoc-Ile-OH, Fmoc-Tyr(tBu)-OH, Fmoc-Pro-OH, Fmoc-Thr(tBu)-OH, Fmoc-Lys(Boc)-OH, Fmoc-Gln-OH and Fmoc-Ala-OH were coupled in sequence by using 100 mg resin. After the completion of coupling, the procedures were carried out upto Step 3 of Schedule 1 to obtain the peptide resin.

To the peptide resin was added 2 ml of Reagent K (5% phenol, 5% thioanisole, 5% H2O, 2.5% ethanedithiol/TEA), and the mixture was reacted at room temperature for 2.5 hours. To the reaction solution was added 10 ml of diethyl ether under ice-cooling. The reaction mixture was stirred for 10 minutes, filtered and washed with 10 ml of diethyl ether. The filter cake was combined with 10 ml of aqueous acetic acid, stirred for 30 minutes and filtered to separate the resin. The resin was washed with 4 ml of aqueous acetic acid. The filtrate and washings were lyophilized, and the resultant crude peptide was dissolved in aqueous acetic acid and loaded onto a reverse phase packing material YMC-PACK ODS-A column (30f×250 nm) pre-equilibrated with 0.1% aqueous TFA. The column was washed with 0.1% aqueous TFA and eluted while increasing the acetonitrile concentration upto 30% over 120 minutes at a flow rate of 7 ml/min. The eluent was monitored at A220 nm and fractions containing the intended substance were collected, lyophilized to obtain 29.3 mg of Ala-Gln-Lys-Thr-Pro-Tyr-Ile-Val-Leu (SEQ ID NO: 6).

The resultant peptide showed retention time of 22.6 minutes when analyzed by a reverse phase packing material SUMIPACK ODS-A211 column (4.6φ×250 nm) eluting with 15 to 45% linear gradient of acetonitrile containing 0.1% TFA. The amino acid analysis and mass spectrometry were consistent with theoretical values.

Amino acid analysis:
Hydrolysis: 1% phenol/6N aqueous hydrochloric acid solution, 110° C., 24 hours
Analytical method: ninhydrin method
 Thr: 0.8 (1)
 Glx: 1.0 (1)
 Ala: 1.1 (1)
 Val: 0.8 (1)
 Ile: 0.8 (1)
 *Leu: 1.0 (1)*reference amino acid
 Tyr: 0.9 (1)
 Lys: 0.9 (1)
 Pro: 0.9 (1)

Theoretical values are indicated in parentheses ( ). Mass spectrometry (FAB) [M +H]$^+$: 1032.5

Example 4

Identification of Tumor Antigen Peptide

To 2×10$^4$ T2 cells (*Immunogenetics*, 21:235,1985), which cell is an HLA-A0201-positive T-B hybridoma cell line but lacks the ability to present endogenous peptides, were added each of six peptides prepared in Example 3 at 10 μM over 2 hours. After incubating with 1×10$^5$ YK-EC for 18 hours, the amount of IFN-γ in supernatant produced by YK-EC was measured by ELISA in the same manner as described in Example 2. The results are shown in Table 4.

TABLE 4

Amount of IFN-γ Produced by YK-EC

| Pulsed Peptide | Amount of INF-γ produced by YK-EC (pg/ml) |
| --- | --- |
| "642–650" | 109.1 |
| "642–651" | 112.4 |
| "650–658" | 118.1 |
| "660–668" | 71.1 |
| "712–720" | 86.1 |
| "778–786" | 105.4 |
| Non peptide | 6.5 |

The results in TABLE 4 suggest that these peptides function as a tumor antigen peptide.

The sililan experiments as the above can be conducted using COS-7 cells (ATCC No. CRL1651) or VA-13 cells (RIKEN CELL BANK) to which HLA-A2 CDNA expression plasmid has been introduced (*J.Exp.Med.*, 187:277, 1998).

The peptides as set forth in SEQ ID NO: 7 to SEQ ID NO: 20 synthesized according to Fmoc method were subjected to the same identification method for tumor antigen peptide as the above. As a result, the peptides described in SEQ ID NO: 7 to SEQ ID NO: 20 were revealed to have an activity as a tumor antigen peptide.

INDUSTRIAL APPLICABILITY

According to the present invention, there can be provided HLA-A2 restricted tumor antigen peptides originated from SART-1, derivatives thereof having characteristics functionally equivalent thereto, therapeutic, prophylactic or diagnostic agents for tumors, which utilize the tumor antigen peptide or its derivative in uivo or in vitro. The therapeutic or prophylactic agents for tumors of the present invention are expected to be useful anti-tumor agents because they can be administered to many patients and are applicable to wide range of tumors of high incidence such as squamous cell carcinomas.

SEQUENCE LISTING FREE TEXT

In the amino acid sequence shown in SEQ ID NO: 35, the second amino acid is leucine, methionine, valine, isoleucine or glutamine, and the ninth amino acid is valine or leucine.

In the amino acid sequence of SEQ ID NO: 36, the second amino acid is leucine, methionine, valine, isoleucine or glutamine, and the tenth amino acid is valine or leucine.

In the amino acid sequence of SEQ ID NO: 37, the second amino acid is leucine, methionine, valine, isoleucine or glutamine, and the ninth amino acid is valine or leucine.

In the amino acid sequence of SEQ ID NO: 38, the second amino acid is leucine, methionine, valine, isoleucine or glutamine, and the ninth amino acid is valine or leucine.

In the amino acid sequence of SEQ ID NO: 39, the second amino acid is leucine, methionine, valine, isoleucine or glutamine, and the ninth amino acid is valine or leucine.

In the amino acid sequence of SEQ ID NO: 40, the second amino acid is leucine, methionine, valine, isoleucine or glutamine, and the ninth minio acid is valine or leucine.

What is claimed is:

1. A tumor antigen peptide consisting of 8–11 amino acid residues, which has an amino acid sequence selected from those each comprising the entire or a partial amino acid sequence(s) of that shown in any one of SEQ ID NO: 1 to SEQ ID NO: 34 and which binds to HLA-A2 antigen and is recognized by cytotoxic T lymphocytes.

2. The tumor antigen peptide according to claim 1, which has an amino acid sequence selected from those each comprising the entire or a partial amino acid sequence(s) of that shown in any one of SEQ ID NO: 1 to SEQ ID NO: 6.

3. A tumor antigen peptide derivative consisting of 8–11 amino acid residues, which has an amino acid sequence selected from those each comprising the entire or a partial amino acid sequence(s) of a sequence wherein the amino acid residue at position 2 and/or C-terminus of the sequence shown in any one of SEQ ID NO: 1 to SEQ ID NO: 34 is replaced by different amino acid, and which binds to HLA-A2 antigen and is recognized by cytotoxic T lymphocytes.

4. The tumor antigen peptide derivative according to claim 3, which has an amino acid sequence selected from those each comprising the entire or a partial amino acid sequence(s) of a sequence wherein the amino acid residue at position 2 and/or C-terminus of the sequence shown in any one of SEQ ID NO: 1 to SEQ ID NO: 6 is replaced by different amino acid.

5. The tumor antigen peptide derivative according to claim 3, which has an amino acid sequence selected from those each comprising the entire or a partial amino acid sequence(s) of a sequence wherein, in the sequence shown in any one of SEQ ID NO: 1 to SEQ ID NO: 34, the amino acid residue at position 2 is replaced by leucine, methionine, valine, isoleucine or glutamine and/or the C-terminal amino acid residue replaced by valine or leucine.

6. The tumor antigen peptide derivative according to claim 5, which has an amino acid sequence selected fom those comprising the entire or a partial amino acid sequence (s) of that shown in any one of SEQ ID NO: 35 to SEQ ID NO: 40.

7. A composition comprising at least one substance selected from the tumor antigen peptides and derivatives thereof according to any one of claim 1, 2, 3, or 4, as an active ingredient.

* * * * *